United States Patent [19]

Wilson

[11] 4,399,070

[45] Aug. 16, 1983

[54] STABLE SALT-FREE PARTIALLY CHELATED METAL COMPOSITIONS AND METHOD OF PREPARATION

[75] Inventor: David A. Wilson, Richwood, Tex.

[73] Assignee: The Dow Chemical Company, Midland, Mich.

[21] Appl. No.: 301,629

[22] Filed: Sep. 14, 1981

[51] Int. Cl.$^3$ .............................................. C07F 3/06
[52] U.S. Cl. .......................... 260/429.9; 260/429 J; 424/289
[58] Field of Search .......................... 260/429.9, 429 J; 424/289

[56] References Cited

U.S. PATENT DOCUMENTS

| | | | |
|---|---|---|---|
| 2,929,681 | 3/1960 | Cardinal et al. ............. | 260/429.9 X |
| 2,952,581 | 9/1960 | Wright ............................. | 424/289 X |
| 2,995,589 | 8/1961 | Leghissa ......................... | 260/429.9 |
| 3,131,048 | 4/1964 | Balassa .......................... | 260/429 J X |
| 3,172,898 | 3/1965 | Wymore ......................... | 260/429.9 X |
| 3,463,858 | 8/1969 | Anderson ....................... | 424/289 |
| 3,681,416 | 8/1972 | Miller et al. ................... | 260/429.9 X |
| 3,719,694 | 3/1973 | Feiler ............................. | 260/429.9 |
| 3,887,704 | 6/1975 | Lichtenstein ................... | 424/289 X |
| 4,152,345 | 5/1979 | Gaudette et al. .............. | 260/429.9 X |

Primary Examiner—Helen M. S. Sneed
Attorney, Agent, or Firm—A. C. Ancona

[57] ABSTRACT

Partially chelated solutions of zinc have been prepared by employing ammonium salts of EDTA together with excess ammonia and dissolving therein an oxide or hydroxide of zinc.

6 Claims, No Drawings

STABLE SALT-FREE PARTIALLY CHELATED METAL COMPOSITIONS AND METHOD OF PREPARATION

BACKGROUND OF THE INVENTION

Aminopolycarboxylic acid chelating agents are well known and employed in combination with various metal ions in the chelated form for a variety of uses. One of the most effective ways of providing micronutrients to plants is to introduce the essential metal ion into the soil in the form of a chelate. Most of these are utilized in the fully chelated form, i.e. one mol of metal ion for each mol of chelant.

In British Pat. No. 1,094,781 there are disclosed compositions in which there is a combination of the metal salt together with the chelate of the same metal. Thus, a metal salt of zinc, e.g. zinc sulfate, was employed together with a zinc chelate, e.g. zinc nitrilotriacetate. An unexpectedly beneficial effect is alleged.

The problem with such salt-containing compositions is that the anions of some salts are phytotoxic, especially the sulfate, and others are undesirable to plants for one reason or another, sometimes depending upon in which part of the country they are to be used. When the zinc nitrilotriacetate is employed in solution, the solution can contain only minor amounts of the chelate since it has a low solubility in water. Thus, the application of zinc as a foliar-spray in this manner would not be practical.

It would, therefore, be desirable if a method could be found for preparing a solution of a zinc compound which would contain no undesirable anions.

It would also be desirable to find a solution of a zinc composition which could be employed as a foliar spray.

Such a solution and a method for preparing it has now been discovered and is the subject of the present invention.

A solution of partially chelated zinc ions has now been prepared by reacting an ammonium salt of ethylenediaminetetraacetic acid (EDTA) with an excess of an oxide or hydroxide of zinc and adding ammonium hydroxide to dissolve the excess unchelated zinc.

Solutions containing zinc/EDTA molar ratios of from 1.01 to 10 have been prepared and a total amount of zinc of up to 10% or more by weight in the solution.

SUMMARY OF THE INVENTION

Partially chelated solutions of zinc have been prepared by employing ammonium salts of EDTA together with excess ammonia and dissolving therein an oxide or hydroxide of zinc.

DETAILED DESCRIPTION OF THE INVENTION

By reacting an ammonium salt of EDTA, preferably the diammonium salt, with zinc oxide, a fully chelated zinc solution can be prepared which contains up to 10% zinc by weight. If excess zinc oxide is added to this it will not dissolve, but if excess ammonium hydroxide is added, the excess zinc will dissolve. Zinc oxide will not, however, dissolve in ammonium hydroxide in the absence of the chelate. Some metals, e.g. Cu, will dissolve in ammonium hydroxide by forming a complex.

While fully chelated solutions of zinc can be prepared from the disodium EDTA and zinc oxide, excess zinc oxide added to such a solution will not dissolve. Such fully chelated solutions can be prepared containing up to about 7% zinc by weight.

The following examples both illustrate the invention and show comparisons with the prior art.

Comparative Example A

Disodium ethylenediaminetetraacetate dihydrate (74.8 g–0.201 mole) and 300 ml. of distilled water were added to a reaction flask equipped with a mechanical stirrer. ZnO (16.4 g–0.200 mole) was added with stirring and the reaction mixture stirred for approximately 1½ hours. The ZnO had all dissolved by this time giving a solution that is fully chelated containing approximately 3.3% zinc by weight.

An additional 4.1 gms of ZnO was added to the chelated solution prepared above. The solution became milky in appearance, typical of undissolved ZnO. The mixture was stirred for about 1½ hours but did not become clear. Ammonium hydroxide (60.1 gms at ~28% $NH_3$) was then added and the mixture stirred for an additional 20 hours at a pH of approximately 12.1. The mixture was milky in appearance with undissolved ZnO present. On standing ZnO settled to the bottom of the flask.

EXAMPLE 1

Ethylenediaminetetraacetic acid (60 gms–0.201 moles), 60 gms of distilled water, and 28.6 gms of ammonium hydroxide (~28% $NH_3$) were added to a reaction flask equipped with a mechanical stirrer. ZnO (16.4 gms–0.200 mole) was added and the reaction mixture stirred for approximately one-half hour. The ZnO had all dissolved by this time giving a solution that is fully chelated containing approximately 8% by weight zinc.

An additional 11 gms of ZnO was added to the chelated solution prepared above. The solution became milky in appearance, typical of undissolved ZnO. The mixture was stirred for an additional 1½ hours but did not clear. Ammonium hydroxide (~28% $NH_3$) was then added to pH 9.5 and stirred for about 10 minutes at which time the reaction mixture became clear. The solution was stirred an additional one-half hour and then water was added to obtain a 10% by weight zinc solution. The Zn/EDTA molar ratio was 1.67.

EXAMPLE 2

Ethylenediaminetetraacetic acid (60 gms–0.201 mole), 45 gms of distilled water, and 48.8 gms of ammonium hydroxide (~28% ammonia) were added to a reaction flask equipped with a mechanical stirrer. ZnO (32.9 gms–0.402 mole) was added and the reaction mixture stirred for about one-half hour. Ammonium hydroxide and water were then added to the milky mixture to obtain a clear solution at pH 10.9 and a zinc concentration of 10% by weight. The Zn/EDTA molar ratio was 2.00.

EXAMPLE 3

Ethylenediaminetetraacetic acid (60 gms–0.201 mole), 30 gms of distilled water, and 48.8 gms of ammonium hydroxide (~28% ammonia) were added to a reaction flask equipped with a mechanical stirrer. ZnO (20.4 gms–0.25 moles) was added and the reaction mixture stirred for approximately one-half hour at which time the ZnO had all dissolved giving a clear solution. The final zinc concentration was 10.2% by weight with a solution pH of about 9.4. The Zn/EDTA molar ratio was 1.25.

Thus, from the above examples it can be seen that one can start with an ammonium salt of EDTA, add sufficient zinc oxide to form a partially chelated mixture, the chelated zinc being in solution, and then add additional ammonium hydroxide to effect solution of the unchelated zinc. Alternatively, one can add sufficient ammonium hydroxide to the EDTA (acid or ammonium salt from) prior to adding the zinc oxide in order to prepare the clear partially chelated solution.

While the examples have employed only the EDTA as illustrative of the aminopolycarboxylic acid, the following amino acids have also been employed to make the partially chelated zinc solutions: N-hydroxyethylethylenediaminetriacetic acid, 1,3 Diaminopropanol-2-tetraacetic acid, 1,3 Diaminopropanetetraacetic acid, Nitrilotriacetic acid, Diethylenetriaminepentaacetic acid, Triethylenetetraaminehexaacetic acid, N-hydroxyethyliminodiacetic acid, Iminodiacetic acid, Ethylenediaminetetrapropionic acid, Nitrilotripropionic acid, and N,N'-ethylenediaminediacetic acid. Anhydrous ammonia can be used instead of $NH_4OH$ and $Zn(OH)_2$ in place of ZnO.

Molar ratios of Zn/chelant of from about 1.01 to about 10 can be employed, but a ratio of about 1.2 to about 5 is preferred.

The amount of ammonia needed for solubilization of greater than stoichiometric amounts of Zn depends on the Zn/chelant molar ratio used, the particular chelant employed, and the zinc concentration in the final solution. Generally the higher the Zn/chelant mole ratio, the greater the amount of ammonia needed for solubilization. The time required for dissolution of the Zn is also dependent on the conditions employed.

The product prepared by the process of the present invention is useful as a foliar spray or in application to the soil to correct zinc deficiencies in crops. The product can be prepared to contain a total amount of zinc ranging from about 1 to about 12% by weight.

I claim:

1. A stable, salt-free partially chelated aqueous zinc solution which contains zinc ions, the zinc chelate of an aminopolycarboxylic acid and ammonium hydroxide, at least part of said zinc ions being unchelated.

2. The solution of claim 1 wherein the molar ratio of zinc to said ammonium salt is from about 1.01 to about 10.

3. The solution of claim 1 wherein the total concentration of zinc in solution is from about 1 to about 12% by weight.

4. The solution of claim 2 wherein the molar ratio is from about 1.2 to about 5.

5. A process for making a stable partially chelated aqueous solution of zinc ions which comprises (1) providing an aqueous solution of an ammonium salt of an aminopolycarboxylic acid, (2) adding thereto in any sequence a molar excess with respect to the aminopolycarboxylic acid salt of an oxide or hydroxide of zinc, and (3) an excess of ammonium hydroxide.

6. A process for making a stable, salt-free partially chelated aqueous solution of zinc ions which comprises (1) providing an aqueous solution of an aminopolycarboxylic acid, (2) adding thereto an excess of ammonium hydroxide, and thereafter (3) an oxide or hydroxide of zinc, the zinc being in molar excess with respect to the aminopolycarboxylic acid.

* * * * *